(12) United States Patent
Halls

(10) Patent No.: US 6,267,949 B1
(45) Date of Patent: Jul. 31, 2001

(54) SUNSCREEN COMPOSITION

(75) Inventor: Neil Graham Halls, Mount Waverley (AU)

(73) Assignee: Soltec Research PTY Ltd. (AU)

( * ) Notice: Subject to any disclaimer, the term of this patent is extended or adjusted under 35 U.S.C. 154(b) by 0 days.

(21) Appl. No.: 09/423,852

(22) PCT Filed: May 20, 1998

(86) PCT No.: PCT/AU98/00373

§ 371 Date: Nov. 15, 1999

§ 102(e) Date: Nov. 15, 1999

(87) PCT Pub. No.: WO98/52525

PCT Pub. Date: Nov. 26, 1998

(30) Foreign Application Priority Data

May 20, 1997 (AU) .................................................. PO6889

(51) Int. Cl.[7] ............................... A61K 7/42; A61K 7/44; A61K 7/00; C01G 9/02

(52) U.S. Cl. ..................... 424/59; 106/14.34; 106/14.39; 106/18.27; 423/621; 423/622; 424/60; 424/400; 424/401

(58) Field of Search ................................ 424/59, 60, 400, 424/401; 106/14.39, 14.34, 18.27; 423/621, 622

(56) References Cited

U.S. PATENT DOCUMENTS

| 5,032,390 | 7/1991 | Iwaya et al. . |
| 5,066,530 | 11/1991 | Kadokura et al. . |
| 5,441,726 | 8/1995 | Mitchnick et al. . |
| 5,575,988 | 11/1996 | Knowles et al. . |
| 5,747,049 | * 5/1998 | Tominaga ............................ 424/401 |

FOREIGN PATENT DOCUMENTS

| 5936594 | 11/1994 | (AU) . |
| 0619999 | 10/1994 | (EP) . |
| WO9213517 | 8/1992 | (WO) . |
| WO9323482 | 11/1993 | (WO) . |
| 9534278 | 12/1995 | (WO) . |
| 9906014 | 2/1999 | (WO) . |
| 9962476 | 12/1999 | (WO) . |

OTHER PUBLICATIONS

Mitchnick, M.A., "Zinc oxide, and old friend to the rescue", Cosmetic and Toiletries, vol. 107, Oct. 1992 (1992–10), pp. 111–116, XP000914123, p. 113, right–hand column, line 3–line 30; figure 2.

* cited by examiner

Primary Examiner—Shelley A. Dodson
(74) Attorney, Agent, or Firm—Ostrolenk, Faber, Gerb & Soffen, LLP

(57) ABSTRACT

The invention provides a sunscreen formulation including conventional UVB sunscreening agents and zinc oxide having an average particle size in the order of 150 to 800 nm. Preferably the zinc oxide used is pigment grade. Most preferably, zinc oxide prepared by the French process is used, although that produced by the American process is also suitable. The average particle size of the zinc oxide is most preferably in the order of 200–400 nm. Throughout this specification, the term "pigment grade" is used to define zinc oxide that has been produced by the French or American process. A further embodiment of the invention is a method of reducing or preventing the harmful effects of solar radiation on skin by applying inventive sunscreen formulation. A further embodiment of the invention relates to a sunscreen composition having a sun protection factor greater than 30 including zinc oxide having an average particle size of 150 to 800 nm. A still further embodiment of the invention relates to a sunscreen composition which is substantially transparent upon application to the skin including zinc oxide having an average particle size of 150 to 800 nm.

21 Claims, 3 Drawing Sheets

Figure 1:
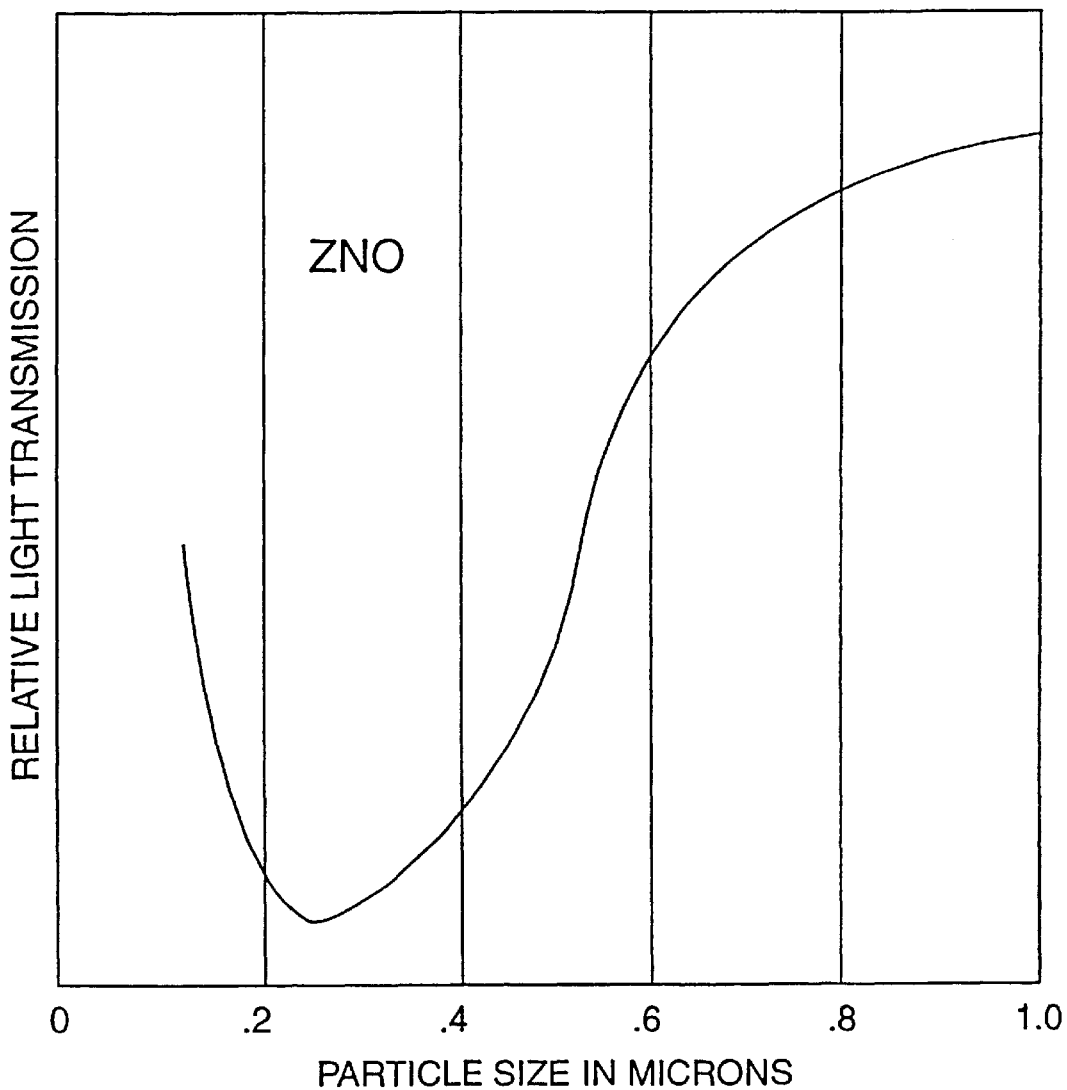

Effect of particle size in visible light transmission of zinc oxide in water suspension.[2]

Effect of particle size in visible light transmission of zinc oxide in water suspension.[2]

Fig 3.

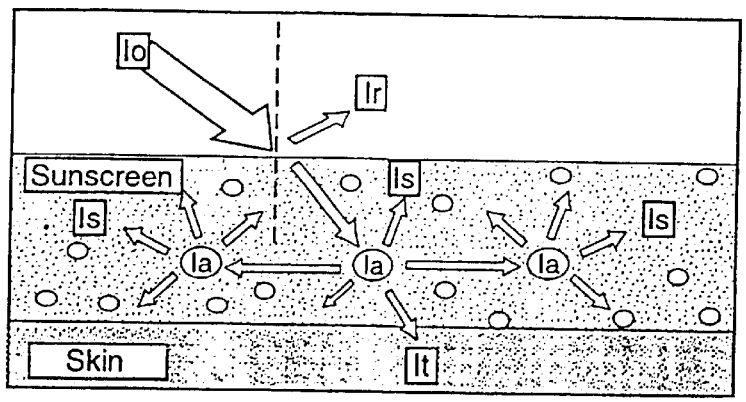

Light scattering behaviour of a sunscreen film

Io = Incident radiation
Ir = specular reflectance from sunscreen surface
Is = radiation scattered by the particle thus not reaching the skin
Ia = radiation absorbed by the particle
It = transmission to the skin (inc. some forward scattered radiation)

For physical sunscreens: $It = Io - (Ir + Ia + Is)$
For organic sunscreens: $It = Io - (Ir + Ia)$

SUNSCREEN COMPOSITION

This invention relates to sunscreen formulations and, more especially to a sunscreen composition including zinc oxide.

In recent years there has been an increasing awareness of the need to use sunscreens for the protection of exposed skin. Solar radiation, in particular that in the ultra-violet region, is considered to be the cause of the painful sunburn, skin discolouration—blotches and freckles and is considered to promote skin aging. In addition, exposure to strong sunlight seems to be a significant contributing factor to skin cancer. It is should be noted that solar ultra-violet radiation contains three types of rays: UV-A, UV-B and UV-C. Whilst the sun's UV-C rays are absorbed by the atmosphere and therefore are not normally a problem, they can be produced in artificial sources, such as arc welding. Zinc oxide provides a high level of UV-ray protection for the skin in the UV-A region. A commercial sunscreen formulation should also provide protection in the UV-B region.

There are many sunscreen formulations known in the pharmaceutical and cosmetic industry. Commercialised formulations are usually in the form of a cream or lotion and contain a number of active components designed to protect the user against various wavelengths of light. In addition these commercial formulations contain further components which provide other desirable aesthetic and technical properties. For example, moisturisers, fragrances and preservatives.

The ability of a sunscreen composition to protect the skin from the harmful effects of the sun is indicated by a sun protection factor (SPF). The higher the SPF the greater the protection afforded by the sunscreen. In Australia, the SPF of a sunscreen product should be evaluated and classified in accordance with the Australian Standard AS/NZS 2604:1993. An SPF rating allows the user to calculate the amount of time he can spend exposed to UV rays without significant deleterious effect. For example an SPF of 4 enables the user to spend 4 times as long in the sun as he normally would before getting sunburnt.

It is well known in the cosmetic industry that various metal oxides have great effect in stopping UV rays from penetrating the skin. In particular, zinc oxide is known for its ability to absorb and scatter UV rays by virtue of Beers Law and its use in sunscreens has been the subject of a number of patent applications. A brief description of the most relevant of these disclosures follows:

AU-B-59365/94 (671189) (Colgate-Palmolive Company) describes a sunscreen composition comprising a water-in-oil emulsion, wherein the oil phase contains nanomised zinc oxide defined in this document as being particles in the range of 10 to 250 nm and polyethylene. The invention is predicated on the discovery of a synergistic interaction between zinc oxide of a particular particle size, polyethylene and normal sunscreening agents such as are described at page 3, lines 6–8.

U.S. Pat. No. 5,032,390 (Kao Corporation) recognises the value of using zinc oxide having a particle size from 70 to 300 nm in sunscreen compositions to scatter or absorb UV rays, particularly those in the UV-A region.

U.S. Pat. No. 5,066,530 (Sumitomo Chemical Company) discloses the use of a lamina comprising a laminar substance as a matrix and zinc oxide (50–500 nm).

U.S. Pat. No. 5,575,988 (Little Point Corporation) describes a combination sunscreen and insect repellent. The sunscreen activity may be provided by using nanomised zinc oxide having a particle size of 300 nm or less.

WO 93/23482 (The Boots Company PLC) describes the preparation of dye coated metal oxides including zinc oxide having a particle size less than 500 nm. These coated metal oxides are used in sunscreen formulations.

In the past it is has been known to use zinc oxide having a larger particle size as a sunscreen agent in "zinc creams". These creams are white or may be coloured with suitable pigments and dyes and retain their colour after application on the skin. They may contain up to 28–32% by weight of zinc oxide. They are normally used in the manner of a face paint, but are not aesthetically acceptable for use over the entire exposed skin area.

Whilst traditional zinc oxide-based sunscreens were thixotropic and non-transparent when applied to the users skin, modern aesthetics demand better feeling and better looking compositions. It is generally thought that in order to provide an aesthetically acceptable sunscreen which is transparent when applied the zinc oxide used must be nanomised. This problem is discussed in AU-B-68039/90 (631704) (Johnson & Johnson Consumer Products, Inc). As noted in that patent only when the zinc oxide particles have an average particle size about, or less than, 50 nanometers do the particles lose their white appearance. A sunscreen formulation using suitably nanomised zinc oxide will be invisible on the skin after application and thus is aesthetically acceptable. Such formulations may contain approximately 4–6% by weight of nanomised zinc oxide.

However, the use of nanomised zinc oxide has disadvantages associated with its high cost which is, in turn transmitted to the cost of the sunscreen. In addition, finely divided particles of zinc oxide tend to agglomerate and this will decrease their SPF rating and produce an inferior product.

It is the objective of the present invention to provide an improved sunscreen formulation which is less expensive and has as high an SPF as possible. It preferably has a long shelf life and is aesthetically acceptable in order to be commercially viable. The sunscreen formulation is ideally cosmetically acceptable, non-toxic and non-irritating to the skin. It should also be controllable in the sense of its spreadability.

The invention provides a sunscreen formulation including conventional UVB sunscreening agents and zinc oxide having an average particle size in the order of 150 to 800 nm. Preferably the zinc oxide used is pigment grade. Most preferably, zinc oxide prepared by the French process is used, although that produced by the American process is also suitable. The average particle size of the zinc oxide is most preferably in the order of 200–400 nm.

Throughout this specification, the term "pigment grade" is used to define zinc oxide that has been produced by the French or American process. French processed zinc oxide is also known as "fumed" zinc oxide by reason of the process steps by which it is achieved. "Coarse" or "BP" grade is another term for the grade of zinc oxide utilised in the invention. The French and American processes are commonly known but are described, for example, in the article Mitchnick, M. A., "Zinc oxide, An Old Friend to the Rescue", *Cosmetics & Toiletries*, Vol 107, October 1992.

The formulations of the invention preferably include one or more metal hydroxystearates The metal hydroxystearates used in the formulations of the invention are preferably magnesium aluminium hydroxystearate and more preferably Gilugel™ brand magnesium aluminium hydroxystearate. The metal hydroxystearate is preferably present in an amount of 2–20% w/w, more preferably, 5–15% w/w.

Preferably, the composition may include active ingredients providing additional protection from light in the UV-A or UV-C regions.

Figure 2:
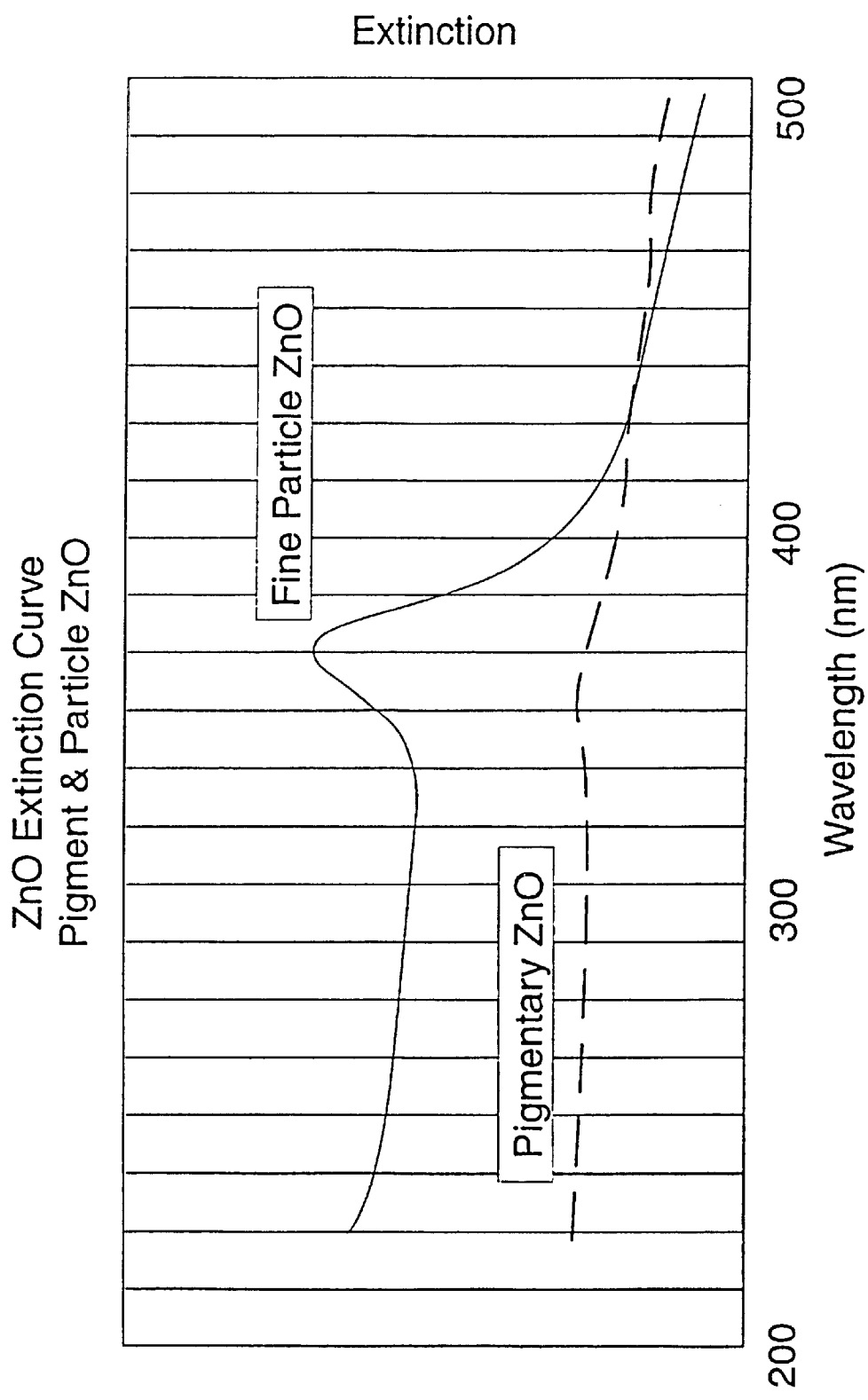

The present invention is partly predicated on the unexpected discovery that when pigment grade zinc oxide is combined with a magnesium aluminium hydroxystearate, in particular Gilugel™, the resultant sunscreen formulation does not retain the expected whiteness or pigmentation after application onto the skin. This significant and surprising advantage is unexpected as pigment grade zinc oxide usually has an average particle size in the order of 100 to 500 nm, results in a generally opaque film and is very visible on the skin when applied as a cream or lotion. Opacity is the ability to prevent light transmission by either reflection and/or absorption. The surface of the zinc oxide crystal effectively reflects visible light. Therefore, the greater the number of surfaces, the more light is reflected. It follows then, that smaller particles, with higher surface area per mass will reflect more light. This appears, however, when particle size versus transmission is plotted, to be not entirely correct. In particular, according to FIG. 1, a graph extracted from Mitchnick, M. A., "Zinc oxide, An Old Friend to the Rescue", *Cosmetics & Toiletries*, Vol 107, October 1992., opacity to visible light reaches a maximum at a particle size of approximately 250 nm. Particles less than this size actually transmit more light. It is postulated that this is because particles smaller than 250 nm, in addition to reflecting light, also scatter it in all directions. Some of this scattered light is transmitted. The sunscreen formulation according to the invention is aesthetically acceptable despite including zinc oxide having a preferred average particle size in the order of 200 to 400 nm which is shown in FIG. 1 to transmit the least light, i.e. be the most opaque. This surprising outcome is further contrasted against existing industry understanding illustrated in FIG. 2 (from Spruce, S. R., "Broad Spectrum protection with "Spectraveil" Zinc oxide and Titanium Dioxide Products—Formulation Efficacy of Zinc oxide", for Tioxide Specialities Ltd at the In-Cosmetics Meeting, Barcelona, 1994) which shows that "Fine Particle" or nanomised zinc oxide has a far higher ability to extinguish light at various wavelengths than does pigment grade zinc oxide.

Secondly, the invention is partly predicated on the discovery that there appears to be synergistic enhancement of the SPF rating provided by a sunscreen formulation containing zinc oxide, a conventional UVB sunscreening agent and metal hydroxystearate. It would normally have been expected that the SPF rating of the overall sunscreen formulation containing zinc oxide, a UVB agent and magnesium aluminium hydroxystearate would be the sum of the effect of agents having sunscreening capacity present in the formulation and in particular the combination of Gilugel™ and zinc oxide and the UVB agent. However, from initial testing, the SPF of the overall sunscreen formulation is significantly higher than that of the sum of the agents having sunscreening capacity.

From a physical perspective, it is theorised that the magnesium aluminium hydroxystearate in its capacity as an oil phase thickener also acts to keep the sunscreen formulation in a layer of sufficient thickness that the Beer-Lambert Law can be exploited to the advantage of the user particularly by the absorption of the UVB light by the UVB screening agent present in the composition. The Beer-Lambert Law states that the intensity of radiation falls off exponentially with the thickness of the sample, and depends on the concentration of the absorbing species, in this case the UVB screening agent, and its ability to absorb light at the frequency being used, in this case, UV light. In particular it is thought that if the path length of the UV light through the formulation can be maximised, the radiation reaching the surface of the skin is minimised. It is thought that the pigment grade zinc oxide performs the function of path light extension. A schematic illustration of this principle, also applicable to titanium dioxide which is commonly used as a sunscreen in adjunct or instead of zinc oxide, is provided by FIG. 3.

A further embodiment of the invention is a method of reducing or preventing the harmful effects of solar radiation on skin by applying the inventive sunscreen formulation. That is a method of reducing or preventing the harmful effects of solar radiation on skin by applying a sunscreen formulation including zinc oxide having an average particle size in the order of 150 to 800 nm. Preferably the zinc oxide used is pigment grade as herein before defined. Preferably the sunscreen formulation will include one or more metal hydroxystearates, more preferably magnesium aluminium hydroxystearate and most preferably Gilugel™ brand magnesium aluminium hydroxystearate. Most preferably the average particle size of the zinc oxide particles is 200–400 nm.

A further embodiment of the invention relates to a sunscreen composition having a sun protection factor greater than 30 including zinc oxide having an average particle size of 150 to 800 nm. Preferably the zinc oxide used is pigment grade as hereinbefore defined. Preferably the sunscreen formulation will include one or more metal hydroxystearates, more preferably magnesium aluminium hydroxystearate and most preferably Gilugel™ brand magnesium aluminium hydroxystearate. Most preferably the average particle size of the zinc oxide particles is 200–400 nm.

A still further embodiment of the invention relates to a sunscreen composition which is substantially transparent upon application to the skin including zinc oxide having an average particle size of 150 to 800 nm. Preferably the zinc oxide used is pigment grade as hereinbefore defined. Preferably the sunscreen formulation will include one or more metal hydroxystearates, more preferably magnesium aluminium hydroxystearate and most preferably Gilugel™ brand magnesium aluminium hydroxystearate. Most preferably the average particle size of the zinc oxide particles is 200–400 nm.

The amount of zinc oxide present in the formulation affects the SPF of the formulation. Whereas nanomised zinc oxide used in prior art formulations is expensive, pigment grade zinc oxide is not, and thus an upper limit is determined for aesthetic reasons only. A minimum amount of pigment grade zinc oxide is required since without it, or in the case where it is not adequately dispersed throughout the formulation, it is found that insufficient diffraction of the light occurs thereby preventing acceptable degrees of absorption of the harmful radiation reaching the surface of the skin. It is preferable that the amount of zinc oxide present be in the range of about 0.05–25% w/w by weight. More preferably the zinc oxide is present in the range of 0.5–15% w/w by weight.

It has also been found that the sunscreen formulations according to the invention are sufficiently waterproof without the addition of a waterproofing polymer such as is required, for example, in the formulations of AU-B-59365/94 (671189) in the name of Colgate Palmolive Company discussed hereinabove.

The sunscreen formulation may be constituted in any form. However, it is preferred that the sunscreen formulation be in the form of an emulsion, more particularly a water-in-oil emulsion. Emulsions are a useful and effective carrier for the zinc oxide. The zinc oxide may be suspended in the oil phase of the emulsion.

The sunscreen formulation is preferably sold in any cosmetically acceptable form, such as a lotion, cream, gel or oil. It is preferred to use an emulsion when producing a sunscreen formulation in the form of a cream, gel or lotion for the purposes of feel and spreadability.

Some examples of ingredients that are active in the UVB region include titanium oxide, oxybenzone, octyl salicylate, octyl methoxycinnamate, octyl dimethyl p-aminobenzoic acid, octocrylene (2-ethylhexyl-2-cyano-3,3-diphenylacrylate), methyl benzylidene camphor, 2-phenyl-benzimidazole-5-sulphuric acid, benzophenone-2, benzophenone-6, benzophenone-12, benzophenone-3, benzophenone-4, benzophenone-8, DEA methoxycinnamate, ethyl dihydroxypropyl PABA, glyceryl PABA, homosalate, menthyl anthranilate, octocrylene, PABA, phenylbenzimidazole sulfonic acid, TEA salicylate, isopropyl dibenzoyl methane, butyl methoxydibenzoylmethane, etocrylene, PEG-25 PABA, octyl triazone, cera bellina wax, filtered yellow beeswax and orange wax. Preferred UVB absorbers according to the invention are octylmethoxycinnamate and methylbenzylidene camphor. These UVB protecting components may be present in an amount of 0–15% w/w, preferably 2.0–8.0% w/w.

In addition known agents having a synergistic affect may also be included to the sunscreen formulation. For example, the use of polyethylene in sunscreen formulations containing zinc oxide and a number of the above sunscreen agents has been shown to synergistically enhance the SPF rating of the overall formulation.

Other known ingredients commonly used in sunscreens may be added to sunscreen formulation of the invention. Examples of such ingredients include emollients, dispersants, emulsifiers, stabilisers, moisturisers, anti-oxidants, preservatives and agents which provide water resistance, enhance skin feel and aid film formation, perfumes and colouring.

Suitable emollients are isopropyl myristate, isopropyl palmitate, liquid paraffin, C12–15 alkyl benzoate, fatty acid esters, triglycerides.

Examples of dispersants include lecithin and solulan PB20.

Any suitable emulsifiers may be used. Example emulsifiers are ethoxylated fatty alcohols, acids and their esters, sorbitan esters, ethoxylated glycerides, glyceryl monostearate, polysorbates, cetyldimethicone copolyols and cyclomethicone/dimethicone polyols. Preferred emulsifiers according to the invention are Arlacel 989™ and Abil WE 09™ which may be present in an amount of 1.0–10% w/w, preferably 2.0–8.0% w/w.

The preferred stabilisers include magnesium sulfate, sodium chloride and sodium citrate.

Preferred moisturisers are glycerin, 1,3-butyleneglycol, propylene glycol, D-panthenol, stearic acid, stearyl alcohol, oleic acid, octyl dodecanol, lanolin and lanolin alcohols and oils and dimethicone silicone.

Various anti-oxidants may be included in the formulation. Examples are butylated hydroxytoluene and tocopherol.

It is also desirable to include one or more preservatives in the formulation. Examples of suitable preservatives include bronopol, imidazolidinyl urea, diazolidinyl urea, sodium dehydroacetate, phenoxyethanol and parabens.

A number of other useful agents may be included in the formulation. For example agents for water resistance such as PVP hexadecene copolymer and silicone oil, agents for enhancement of skin feel such as cyclomethicone and agents for aiding film formation such as polyethylene and alkylated polyvinylpyrrolidone.

EXAMPLES OF THE INVENTION

The invention is further illustrated by, but is not limited to, the following examples.

Example 1

A trial formulation was prepared by combining pigment grade zinc oxide (10% by weight) with octyl methoxycinnamate (7.5% by weight). The formulation was found to have a pre-swim SPF (measured in accordance with the standard hereinbefore referred to) of 41.

Examples 2–7

Trial formulations were prepared according to the following table, and pre-swim SPF (measured as hereinbefore described) measured. Results are also tabulated.

| Example No./ Ingredient | 2 % w/w | 3 % w/w | 4 % w/w | 5 % w/w | 6 % w/w | 7 % w/w |
|---|---|---|---|---|---|---|
| Arlacel 989 | — | — | — | 7.0 | 7.0 | 7.0 |
| Abil WE 09 | 3.0 | 5.0 | 5.0 | — | — | — |
| Finsolv TN | 6.5 | 6.5 | 6.5 | 6.5 | 6.5 | 6.5 |
| Octylmethoxy-cinnamate | — | — | 7.5 | 7.5 | 7.5 | 7.5 |
| Methyl-benzylidene camphor | 4.0 | 4.0 | — | — | — | — |
| Isopropyl palmitate | 16.0 | 16.0 | 17.5 | 15.5 | 17.7 | 10.6 |
| Paraben ester | 0.3 | 0.3 | 0.3 | 0.3 | 0.3 | 0.1 |
| Gilugel OS | 11.0 | 11.0 | 11.0 | 11.0 | — | 11.0 |
| Propylene glycol | 2.0 | 2.0 | 2.0 | 2.0 | 2.0 | 2.0 |
| Phenoxy-ethanol | 0.6 | 0.6 | 0.6 | 0.6 | 0.6 | 0.6 |
| Methyl Paraben | 0.1 | 0.1 | 0.1 | 0.1 | 0.1 | 0.1 |
| Water | 56.5 | 44.1 | 44.1 | 44.1 | 44.1 | 44.1 |
| Zinc oxide | — | 10.0 | 5.0 | 5.0 | 5.0 | 10.0 |
| Sodium chloride | — | — | 0.4 | 0.4 | 0.4 | — |
| Octyl stearate | — | — | — | — | 8.8 | — |
| Magnesium Sulphate | — | — | — | — | — | 0.5 |
| Preswim SPF | 16.0 | >39.4 | >41.3 | 34.2 | 14.1 | 41.3 |

It will be appreciated that example 2 in which no pigment grade zinc oxide is present has a relatively low SPF of 16.0. Example 6, incorporating no metal hydroxystearate, but 5% w/w zinc oxide has an SPF of 14.1 whereas example 5 including both 5% w/w zinc oxide and 11% w/w Gilugel™ has an SPF of 34.2. All formulations are transparent when applied to the skin of the user.

The commercial form of the formulation according to the invention (example 4) containing 7.5% octylmethoxycinnamate and 5.0% pigment grade Zinc oxide produces a pre-swim SPF of greater than 41.3, a post swim SPF (after 2 hours of water immersion) of greater than 38.9, and a post swim SPF (after 4 hours of water immersion) of 31.

Examples 8–12

Tabulated below are examples in which the formulations were identical other than in respect of the percent w/w of the zinc oxide present in the formulations. In each formulation a UVB agent has been used as has a metal hydroxystearate. The SPF has been generated by testing on human subjects.

| Example Number | % w/w Pigment Grade Zinc oxide | SPF Rating |
|---|---|---|
| 8 | 0.5 | 25.0 |
| 9 | 1.0 | 28.2 |
| 10 | 2.0 | 25.0 |
| 11 | 4.0 | 41.5 |
| 12 | 3.0 + 2.0% silicone coated nanomised zinc oxide | 25.0 |

The 5% pigment grade zinc oxide sunscreen composition according to the invention produces an SPF of 41 or more, as does the 4% pigment grade zinc oxide sunscreen of example 11 in the table hereinabove. It is evident that the addition of silicone coated nanomised zinc oxide in example 12 may in fact subtract from the SPF of the formulation rather than add to it. It is also evident that nanomised zinc oxide does not serve to diffract the UV light as apparently pigment grade zinc oxide does. A very small amount of pigment grade zinc oxide (0.5%), it is shown can substantially boost the SPF of the formulation.

Examples 13–15

As an alternative to octylmethoxycinnamate used in examples 4–7, tests were also conducted using Methyl Benzylidene Camphor (MBC) as the UVB absorbing sunscreen component. SPF ratings were determined by application of the formulations to humans, which were identical but for the indicated variations and include magnesium aluminium hydroxy stearate.

| Example Number | % w/w Zinc oxide | % MBC | SPF Rating Pre Swim | Post Swim 2 hrs |
|---|---|---|---|---|
| 13 | 10.00 | 4 | >39.4 | 37.7 |
| 14 | 0 | 4 | 16.0 | |
| 15 | 5.0 | 4 | 28.0 | |

It is thus shown that the presence of the pigment grade zinc oxide in formulations in adjunct with a UVB absorbing compound and magnesium aluminium hydroxystearate elicits SPFs which are substantially higher than those pertaining to formulations in which there is no pigment grade zinc oxide present.

Examples 16–19

These examples demonstrate the apparent synergy occurring between the metal hydroxystearate, the pigment grade zinc oxide and the UVB absorbing agent in the compositions according to the invention. Example 16 is absent the UVB absorbing agent. It is postulated that in this instance, the composition is able to diffract the UV light but unable to absorb it because of the absence of the UVB absorbing component. Example 17 demonstrates the absence of the metal hydroxystearate. In this instance, it is thought that the physical structure of the formulation collapses, and little or no absorption can occur. Example 18 demonstrates the absence of pigment grade zinc oxide. In this instance, nothing in the formulation acts to diffract the light through the formulation. It can be seen in example 19 that the total formulation gives an SPF far superior to the additive effects of the three components.

| Ingredient | Example 16 % w/w | Example 17 % w/w | Example 18 % w/w | Example 19 % w/w |
|---|---|---|---|---|
| Abil WE 09 | 5.0 | 5.0 | 5.0 | 5.0 |
| Finsolv TN | 6.5 | 6.5 | 6.5 | 6.5 |
| Octylmethoxycinnamate | 0.0 | 7.5 | 7.5 | 7.5 |
| Isopropyl palmitate | 25.0 | 19.7 | 22.5 | 17.5 |
| Paraben esters | 0.3 | 0.3 | 0.3 | 0.3 |
| Gilugel OS | 11.0 | 0.0 | 11.0 | 11.0 |
| Octyl Stearate | 0.0 | 8.8 | 0.0 | 0.0 |
| Propylene glycol | 2.0 | 2.0 | 2.0 | 2.0 |
| Phenoxyethanol | 0.6 | 0.6 | 0.6 | 0.6 |
| Methyl paraben | 0.1 | 0.1 | 0.1 | 0.1 |
| Water | 44.1 | 44.1 | 44.1 | 44.1 |
| Zinc oxide | 5.0 | 5.0 | 0.0 | 5.0 |
| Sodium chloride | 0.4 | 0.4 | 0.4 | 0.4 |
| Total | 100 | 100 | 100 | 100 |
| Preswim SPF | 3.4 | 12.8 | 16.0 | >41.3 |

It will be appreciated by a skilled addressee that a number of other ingredients may be included in the formulations and the invention includes such formulations. Furthermore, a number of the above ingredients may be replaced by commonly accepted substitute ingredients. The invention also includes formulations wherein substitute ingredients have been used. Finally, as stated above the examples illustrate but do not limit the present invention.

The claims defining the invention are as follows:

1. A sunscreen formulation including at least one UVB sunscreening agent, zinc oxide having an average particle size of 150 to 800 nm, and at least one metal hydroxystearate in a synergistically effective amount.

2. A sunscreen formulation as claimed in claim 1 wherein said zinc oxide is pigment grade zinc oxide.

3. A sunscreen composition as claimed in claim 1 wherein said metal hydroxystearate is magnesium aluminum hydroxystearate.

4. A sunscreen composition as claimed in claim 1 wherein said metal hydroxystearate is present in an amount of 2–20% w/w.

5. A sunscreen composition as claimed in claim 1 wherein said UVB sunscreening agent is selected from the group consisting of octyl methoxycinnamate and methylbenzylidene camphor.

6. A sunscreen composition as claimed in claim 1 wherein said zinc oxide is present in an amount of 0.05–25% w/w.

7. A sunscreen composition as claimed in claim 1 wherein said zinc oxide is present in an amount of 0.5–15% w/w.

8. A sunscreen composition as claimed in claim 1 comprising pigment grade zinc oxide, octyl methoxycinnamate and magnesium aluminum hydroxystearate.

9. A sunscreen composition as claimed in claim 1 wherein the average particle size of the zinc oxide is 200–400 nm.

10. A sunscreen composition having the sun protection factor greater than 30 including zinc oxide having an average particle size of 150 to 800 nm and at least one metal hydroxystearate in a synergistically effective amount.

11. A sunscreen composition as claimed in claim 10 wherein said zinc oxide is pigment grade.

12. A sunscreen composition which is substantially transparent upon application to the skin including zinc oxide having an average particle size of 150 to 800 nm and at least one metal hydroxystearate in a synergistically effective amount.

13. A sunscreen composition as claimed in claim 12 wherein said zinc oxide is pigment grade and said metal hydroxystearate is magnesium aluminium hydroxystearate.

14. A method of reducing or preventing the harmful effects of solar radiation on skin by applying to skin requiring such treatment of sunscreen formulation including zinc oxide having an average particle size in order of 150 to 800 nm and at least one metal hydroxystearate in a synergistically effective amount.

15. A method as claimed in claim 14, wherein said zinc oxide is pigment grade and said metal hydroxystearate is magnesium aluminium hydroxystearate.

16. A sunscreen composition as claimed in claim 14 wherein said metal hydroxystearate is magnesium aluminum hydroxy stearate.

17. A sunscreen composition as claimed in claim 14 wherein said metal hydroxystearate is present in an amount of 2–20% w/w.

18. A sunscreen composition as claimed in claim 14 wherein said zinc oxide is present in an amount of 0.05–25% w/w.

19. A sunscreen composition as claimed in claim 10 wherein said metal hydroxystearate is magnesium aluminum hydroxystearate.

20. A sunscreen composition as claimed in claim 10 wherein said metal hydroxystearate is present in an amount of 2–20% w/w.

21. A sunscreen composition as claimed in claim 10 wherein said zinc oxide is present in an amount of 0.05–25% w/w.

* * * * *